April 13, 1971 R. BANTA Plant Pat. 3,045
APPLE TREE
Filed June 18, 1969
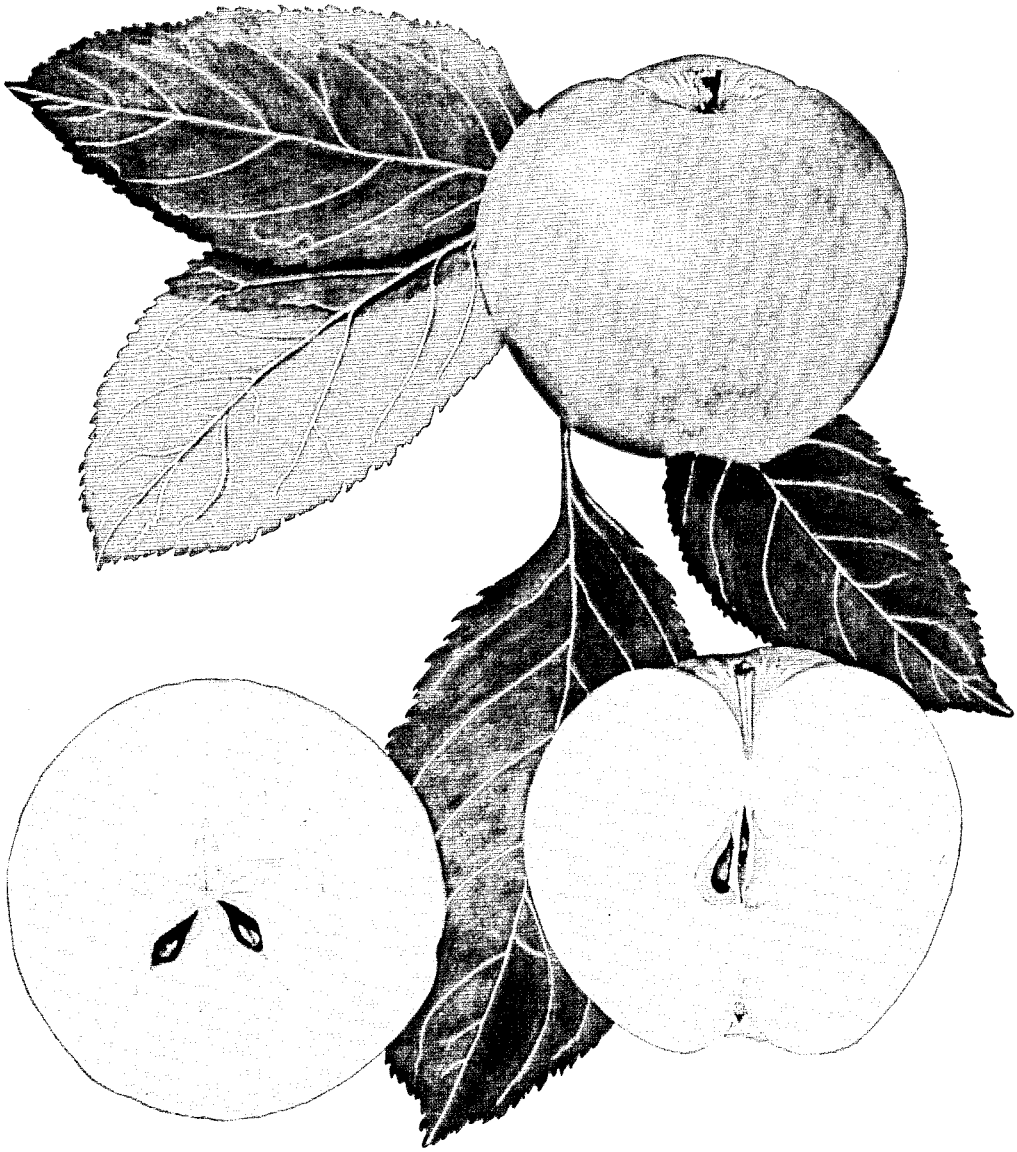
INVENTOR:
RALPH BANTA
WITNESS: Ruth Ingeborg Andris
BY: Cummings and Snow
ATTYS.

United States Patent Office

Plant Pat. 3,045
Patented Apr. 13, 1971

3,045
APPLE TREE

Ralph Banta, Green Forest, Ark., assignor to Merle J. Lucas, doing business as Green Forest Nursery, Green Forest, Ark.

Filed June 18, 1969, Ser. No. 834,564
Int. Cl. A01h 5/03
U.S. Cl. Plt.—34 1 Claim

ABSTRACT OF THE DISCLOSURE

This disclosure concerns a new and distinct variety of apple tree characterized by the fruit having a dark red uniform color and having an elongated shape with heavier stems than the Jonathan tree.

BACKGROUND OF INVENTION

This new and distinct variety was discovered by me on my orchard in Green Forest, Ark. (Route 1). About 50 to 60 cuttings have been taken from the parent tree and propagated and interplanted with various other varieties of apple trees, and are producing abundantly, true to form every year. The apples ripen two weeks to a month ahead of Jonathan apples and are redder in color and larger, and having a tartness, slightly similar to a Jonathan apple. Each year, since 1950, the tree has had the same growing habits and same fruit.

DESCRIPTION OF DRAWING

The accompanying drawings, in full color, show typical examples of fruit and foliage of my new variety of apple tree, the fruit being shown in axial and transverse cross section as well as in elevation.

DESCRIPTION OF THE NEW PLANT VARIETY

The following is a detailed description of my new variety with the color designations according to Maerz and Paul's "A Dictionary of Color."

Origin: Seedling.
Parentage: Unknown.
Classification: Hybrid.
Growth habit: Vigorous, upright, hardy and very fast growth habit during the first 5 years, at which time the growth slows down.
Height: Semi Dwarf, 18 to 20 feet.
Trunk: Thick and heavy, from ground up about 10 inches.
Branches: Very heavy and vigorous extending outwardly at an angle of 50 to 60 degrees.
Leaves: Abundant and large.
Size: Length—4 to 6"; width—1½ to 2½".
Shape: Ovate.
Margin type: Deltoid, serrated.
Color: Upperside—Plate 12, L–4; underside—Plate 21, G–4.

Lenticels: Large and abundant.
Flowers: About mid-April in northern Arkansas with larger blossoms than the Jonathan apple tree, having creamy pink color.
The fruit:
*Shape.*—Oblong ovoid, generally symmetrical.
*Size.*—About 3 inches diameter and about 3 inches high.
Color: Overall dark red, Plate 4, L–6 with relatively small spots Plate 9, 11 appearing sporadically on surface. Area around stem base, Plate 18, J–2.
Stem: About ¾ inch long.
Color: Plate 7, E–10 with overtones of Plate 8, H–7. Base of stem, Plate 13, L–1.
Cavity: About ½ inch deep and approximately 1¼ inches wide.
Basin: About ⅜ inch deep and about ⅜ inch wide.
Core: Seed cavity.—About 1 to 1⅛ inches wide and about 1 inch long. Color: Plate 9, F–1. Seeds—About ⅜ inch long and ⅛ inch wide and thick. Color Plate 12, L–10 and shaded outwardly to Plate 12, C–11 and Plate 8, C–6.
Flesh: Firm in texture, juicy and tart. Crunchy when eaten.
Aroma: Very pleasant and predominant.
Color: Slightly off-white.
Maturity season: In northern Arkansas from August 1st to 10th.
Taste: Tart, acid, tangy, somewhat sweet.
Keeping quality: Fair.
Use: Excellent eating apple. Very good for juice, cooking and canning. Apple when cooked stays in piece form and not reduced like apple sauce.

In particular my new variety of apple is distinguished by its deep overall red color. It ripens approximately two weeks before the Jonathan apple, has fair keeping quality and is particularly good for both eating and cooking purposes because of its pleasant taste and aroma which persists through the cooking process. The plant is distinguished by its rapid growth and by its high production of fruit of a size larger than the Jonathan. The branches grow from 18 to 24 inches of new wood each year. The variety is resistant to scab and blotch. Having thus described my new variety of apple tree, I claim:

1. A new and distinct variety of apple tree as shown and described, particularly characterized as to novelty by the large size, deep red color with the tart taste of Jonathan apple, by the early maturity season for its fruit, by the abundance of fruit each year and by the persistent pleasing aroma of the fresh fruit and throughout cooking and canning process.

No references cited.

ROBERT E. BAGWILL, Primary Examiner